United States Patent [19] [11] 4,073,917
Sandberg et al. [45] Feb. 14, 1978

[54] LOCAL ANESTHETICS TERTIARY AMINOALKOXYPHENYL ETHERS

[75] Inventors: Rune Verner Sandberg, Jarna; Sven Bengt Arvid Åkerman, Sodertalje, both of Sweden

[73] Assignee: Astra Läkemedel Aktiebolag, Sodertalje, Sweden

[21] Appl. No.: 641,984

[22] Filed: Dec. 18, 1975

[30] Foreign Application Priority Data

Dec. 20, 1974 Sweden .............................. 7416143

[51] Int. Cl.² .................... A61K 31/445; C07C 91/28; C07D 295/08
[52] U.S. Cl. ............................ 424/267; 260/293.83; 260/326.5 M; 260/570.7; 424/274; 424/330
[58] Field of Search ................... 260/293.83, 326.5 M, 260/570.7; 424/267, 274, 330

[56] References Cited

U.S. PATENT DOCUMENTS 2,967,201 1/1961 Soper ................................. 260/570.7
3,175,006 3/1965 Druey et al. ...................... 260/570.7
3,904,622 9/1975 Thominet ......................... 260/247.7 S

FOREIGN PATENT DOCUMENTS 213,872 3/1961 Austria .......................... 260/570.7 R
879,342 10/1961 United Kingdom .......... 260/570.7 R

OTHER PUBLICATIONS

Wright et al., J. Amer. Chem. Soc. 1951, vol. 73, pp. 2281–2283.

Primary Examiner—Natalie Trousof
Attorney, Agent, or Firm—Brumbaugh, Graves, Donohue & Raymond

[57] ABSTRACT

A compound of the formula

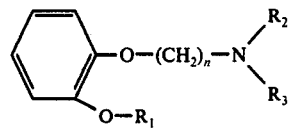

and pharmaceutically acceptable acid addition salts thereof, in which $R_1$ represents an alkyl group selected from n-propyl, i-propyl, n-butyl, i-butyl and sek.butyl, $R_2$ and $R_3$ are the same or different and represent an alkyl group selected from ethyl, n-propyl, and i-propyl, or $R_2$ and $R_3$ together with the nitrogen atom may form a pyrrolidine or piperidine ring, and $n$ is 2 or 3. Pharmaceutical preparations containing these compounds are useful as local anesthetics.

21 Claims, No Drawings

LOCAL ANESTHETICS TERTIARY AMINOALKOXYPHENYL ETHERS

The present invention relates to novel local anesthetic compounds of the type tertiary aminoalkylphenyl ethers.

Secondary aminoalkylphenyl ethers containing a lower alkoxy groups, such as methoxy or ethoxy, in orto-position have been described in the U.S. Pat. Nos. 2,967,201 and 3,175,006. These compounds are said to have central depressant action and, respectively, sympaticolytic and sedative activity.

Some tertiary aminoalkylphenyl ethers containing a lower alkoxy group in orto-position have been described in J.A.C.S. 73, 2281–83 (1951). The compound o-methoxy-(diethylaminoethoxy)-benzene can be mentioned as an example. The said compound is mentioned as a member of a group of compounds asserted to exhibit some degree of local anesthetic activity. However, none of the compounds showed particular advantage over an old reference compound; and as a matter of fact we have not been able to find any local anesthetic activity for the compound o-methoxy-(diethylaminoethoxy)-benzene According to the present invention it has surprisingly been found that a certain group of novel tertiary aminoalkylphenyl ethers, containing an alkoxy group with 3-4 carbon atoms in onto-position, exhibit excellent local anesthetic activity particularly as to depth and duration of action. The new compounds are especially useful for surface anesthesia and for long-lasting infiltration and regional anesthesia and they have a satisfactory low acute toxicity.

The compounds of the present invention have the structural formula

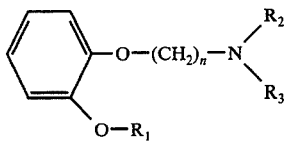

wherein $R_1$ represents an alkyl group selected from n-propyl, i-propyl, n-butyl, i-butyl and sec.-butyl, $R_2$ and $R_3$ are the same or different and represents an alkyl group selected from ethyl, n-propyl and i-propyl, preferably i-propyl, or $R_2$ and $R_3$ together with the nitrogen atom may form a pyrrolidine or piperidine ring, and $n$ is 2 or 3, preferably 2, including pharmaceutically acceptable acid addition salts thereof.

An especially valuable sub-group of compounds of the formula I is obtained when $R_1$ is selected from n-propyl, n-butyl and i-butyl, and $R_2$ and $R_3$ are the same and are selected from ethyl and i-propyl. Two compounds of this type, viz 1-n-butoxy-2-(2'-diisopropylaminoethoxy)-benzene and 1-n-propoxy-2-(2'-diisopropylaminoethoxy)-benzene, can be mentioned as examples of compounds being particularly preferred.

Other compounds included in the invention are for example, 1-isobutoxy-2-(2'-diisopropylaminoethoxy)-benzene, 1-isobutoxy-2-(2'-diethylaminoethoxy)-benzene, 1-isobutoxy-2-(3'-diethylaminopropoxy)-benzene, 1-n-propoxy-2-(3'-diisopropylaminopropoxy)-benzene, 1-n-butoxy-2-(3'-diethylaminopropoxy)-benzene, 1-n-butoxy-2-(2'-piperidinoethoxy)-benzene, 1-n-butoxy-2-[2'-ethyl-isopropylaminoethoxy]-benzene, 1-n-butoxy-2-[3'-ethyl-isopropylaminopropoxy]-benzene, and 1-n-butoxy-2-(2'-pyrrolidinoethoxy)-benzene.

The compounds of the invention can be prepared by a. reacting a phenol of the formula

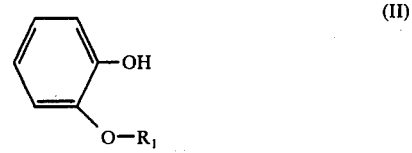

with a reactive ester of an alcohol of the formula

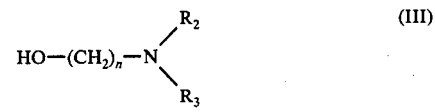

in the presence of a condensating agent, in which formulas $R_1$, $R_2$, $R_3$ and $n$ have the meaning given above; or b. reacting a compound of the formula

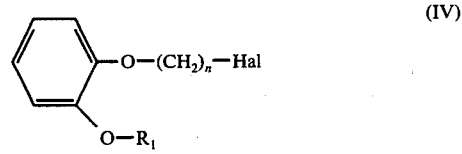

with an amine of the formula

in which formulas $R_1$, $R_2$, $R_3$ and $n$ have the meaning given above, and Hal is bromine or chlorine.

In method a the reactive ester is preferably an ester obtained with a strong inorganic acid, such as hydrochloric acid or hydrobromic acid. The reaction is preferably carried out in an organic solvent, such as e.g. ethanol, at a raised temperature under atmospheric pressure. Preferably the reaction is carried out at the boiling point of the applied solvent. The condensating agent used may be e.g. sodiumethoxide. The condensation may alternatively be performed as an extractive alkylation.

The process according to method b is preferably carried out in an organic solvent, such as e.g. toluene, at a raised temperature under atmospheric pressure. Preferably the reaction is carried out at the boiling point of the applied solvent.

The intermediate of the formula IV is a novel compound and constitutes a further aspect of the invention. Said intermediate can be prepared by methods known per se, e.g. by reacting a compound of the formula (II) with a compound of the formula Hal—$(CH_2)_n$—Hal, in which formulas $R_1$, Hal and $n$ have the meaning given above.

Depending on the starting materials and the reaction conditions used, the new compounds are obtained in the free form or in the form of salts, which also form part of this invention. The salts of the new compounds can be transformed to known manner into the free bases; for example by reaction with a basic agent or an ion exchanger. On the other hand, the resulting free bases may form salts with inorganic or organic acids.

The compounds of the invention are useful as local anesthetics in the conventional manner and employing conventional dosages thereof. These bases may be conventionally used in the form of solutions of their pharmaceutically acceptable salts, e.g. the hydrochlorides, tartrates and citrates.

Parenteral solutions can be administered peridurally, subarachnoidally and by infiltration. Solutions, ointments and sprays prepared from the bases or pharmaceutically acceptable salts thereof can be administered topically to mucous membranes and injured, e.g. abraded or intact skin.

At parenteral administration the compounds can be used in concentrations from 0.25–2% by weight, and in doses from 75–300 mg. The concentrations and doses are, however, not restricted to these ranges, but have to be determined individually with consideration taken to factors such as the age and the body weight of the patient, the clinical indication and the route of administration. For example at topical administration to intact skin it is preferred to use a concentration from 5–15% by weight. At such administration it is particularly preferred to use the base form, dissolved in a solvent consisting of isopropanol (40–80 volume-%), glycerol (0–20 volume-%) and water (10–50 volume-%).

The invention will be further illustrated by the following examples:

EXAMPLE 1

1-n-Butoxy-2-(2'-diisopropylaminoethoxy)-benzene

To 750 ml of absolute ethanol was added gradually 13.8 g (0.60 mole) of metallic sodium cut into pieces. After all the sodium had reacted 49.8 g (0.30 mole) of o-butoxyphenol was added. The solution was cooled down in ice-water whereupon a solution of 60.0 g (0.30 mole) of diisopropylaminoethylchloride hydrochloride in 150 ml of absolute ethanol was added rapidly with stirring. The reaction mixture was then boiled under reflux for 5 hours.

The salts were removed by suction filtration and the filtrate stripped of solvent at reduced pressure. The residue was dissolved in ether, the ether solution washed once with water and was then extracted with an excess of dilute hydrochloric acid. The extracts were made alkaline with concentrated sodium hydroxide solution and the precipitated base was extracted twice with ether. The ether extracts were dried over potassium carbonate. Evaporation and destillation gave 73.4 g (83%) of pure product (according to GC analysis) boiling at 123–124° C, under a pressure of 0.005 mmHg, $n_D^{25}$: 1.4940. Calcd. for $C_{18}H_{31}NO_2$: C 73.67%, H 10.65%, N 4.77%: Found C 73.6%, H 10.5%, N 4.60%.

The hydrochloride, recrystallized from ethyl acetate, had m.p. 100.5–2.5° C. Calcd. for $C_{18}H_{32}NO_2Cl$: Cl 10.75%; Found Cl 10.8%.

EXAMPLE 2

1-n-Propoxy-2-(2'-diisopropylaminoethoxy)-benzene

The compound was prepared as described in Example 1, using sodium (3.45 g; 150 mole), 0-propoxyphenol (11.4 g; 75 mmole) and diisopropylaminoethylchloride hydrochloride (15.0 g; 75 mmole) in 200 ml of ethanol. Yield 12.7 g (64%) of product, boiling at 109°–110° C under a pressure of 0.001 mm.Hg, $n_D^{25}$: 1.4961. Calcd. for $C_{17}H_{29}NO_2$: C 73.07%, H 10.46%, N 5.01%. Found C 73.2% H 10.5%, N 4.96%.

EXAMPLE 3

1-Isobutoxy-2-(2'-diisopropylaminoethoxy)-benzene

The compound was prepared as described in Example 1, using sodium (3.45 g; 150 mmole), o-isobutoxyphenol (12.45 g; 75 mmole) and diisopropylaminoethylchloride hydrochloride (15.0 g; 75 mmole) in 200 ml of ethanol. Yield 11.2 g (51%) of product, boiling at 111°–113° C under a pressure of 0.001 mm.Hg, $n_D^{25}$: 1.4920.

Calcd. for $C_{18}H_{31}NO_2$ : C 73.67%, H 10.55%, N 4.77%. Found C 73.7%, H 10.7%, N 4.91%.

EXAMPLE 4

1-Isobutoxy-2-(2'-diethylaminoethoxy)-benzene

The compound was prepared as described in Example 1, using sodium (2.3 g; 100 mole), o-isobutoxyphenol (8.30 g; 50 mmole) and diethylaminoethylchloride hydrochloride (8.6 g; 50 mmole) in 150 ml of ethanol. Yield 9.3 g (70%) of product, boiling at 112° C under a pressure of 0.01 mm Hg, $n_D^{25}$: 1.4942.

Calculated for $C_{16}H_{27}NO_2$: C 72.41%, H 10.26%, N 5.28%. Found: C 72.3%, H 10.4%, N 5.30%.

EXAMPLE 5

1-Isobutoxy-2-(3'-diethylaminopropoxy)-benzene

The compound was prepared as directed in Example 1, using sodium (1.15 g; 50 mole), o-isobutoxyphenol (8.30 g; 50 mmole) and 3-diethylaminopropylchloride (7.50 g; 50 mmole) in 150 ml of ethanol. Yield 8.85 g (63%) of product, boiling at 104°–106° C under a pressure of 0.003 mm Hg, $n_D^{25}$: 1.4914.

Calculated for $C_{17}H_{29}NO_2$: C 73.07%, H 10.46%, N 5.01%. Found: C 72.8%, H 10.6%, N 4.95%.

EXAMPLE 6

1-n-Butoxy-2-(2'-piperidinoethoxy)-benzene

The compound was prepared as described in Example 1, using sodium (2.3 g, 100 mmole), o-butoxyphenol (8.30 g, 50 mmole) and piperidinoethylchloride hydrochloride (9.2 g, 50 mmole) in 150 ml of ethanol. Yield 4.4 g (32%) of product boiling at 121° C under a pressure of 0.02 mm Hg; $n_D^{25}$ 1.5135.

Calc. for $C_{17}H_{27}NO_2$: C 73.60%, H 9.81%, N 5.05%. Found: C 72.8%, H 9.71%, N 5.13%.

EXAMPLE 7

1-n-Butoxy-2-(2'-diisopropylaminoethoxy)-benzene

The compound was prepared according to method b) using 1-n-butoxy-2-(2'-bromoethoxy)-benzene as a starting material. The starting material was prepared by adding a solution of sodium hydroxide (4 g; 10 mmole) and tetrabutylammoniumhydrogensulphate (17 g, 50 mmole) in water (50 ml) with stirring to a solution of o-butoxyphenol (8.3 g 50 mmole) in 1,2-dibromoethane (50 ml). pH of the reaction mixture was maintained at 12 throughout the reaction by dropwise addition to 15-N sodium hydroxide solution; 8 ml had been added when the reaction was completed after 2.5 hours. The organic layer was separated, washed with water and dried over magnesiumsulphate. Destillation gave 9.55 g of product with b.p 96° C at 0.03 mm Hg. MS: M + m/e 272/274 basepeak m/e 107/109

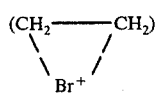

The thus obtained 1-n-butoxy-2-(2'-bromoethoxy)-benzene (2.73 g, 10 mmole) was heated under reflux for 160 hours with diisopropylamine (4.0 g; 40 mmole) and toluene (25 ml). The reaction mixture was shaken with water until the precipitated salt had dissolved. The toluene phase was then extracted with an excess of dilute hydrochloric acid. The extracts were washed twice with ether and then made alkaline with sodium hydroxide solution. The precipitated base was taken up in ether and the aqueous phase extracted once more with ether. The ether extracts were washed once with water and then dried over potassium carbonate. The solvent was evaporated and the residue distilled to yield 1.57 g (53.5%) of product with b p 104°–105° C at 0.02 mm Hg; $n_D^{25} = 1.4936$.

EXAMPLE 8

This example illustrates pharmaceutical compositions for infiltration anesthesia. Solutions containing 0.25, 0.50, 0.75 and 1.0% 1-n-butoxy-2-(2'-diisopropylaminoethoxy)-benzene hydrochloride without added vasoconstrictor may be prepared by mixing according to the following table:

| Component | Amount (g) 0.25% | 0.50% | 0.75% | 1.0% |
| --- | --- | --- | --- | --- |
| 1-n-Butoxy-2-(2'-diisopropyl aminoethoxy)benzene hydrochloride | 2.50 | 5.00 | 7.50 | 10.00 |
| Sodium Chloride USPXVIII | 8.53 | 8.07 | 7.70 | 7.10 |
| Hydrochloric acid, 2N | If necessary to adjust pH | | | |
| Sodium hydroxide, 2N | If necessary to adjust pH | | | |
| Water for injection, USPXVIII | Sufficient amount to make 1000 ml | | | |

EXAMPLE 9

This example illustrates pharmaceutical compositions for infiltration anesthesia. Solutions containing 0.25, 0.50, 0.75 and 1.0% 1-n-butoxy-2-(2'-diisopropylaminoethoxy)-benzene hydrochloride and epinephine 1:200.000 may be prepared by mixing according to the following table:

| Component | Amount (g) 0.25% | 0.50% | 0.75% | 1.0% |
| --- | --- | --- | --- | --- |
| 1-n-Butoxy-2-(2'-diisopropylaminoethoxy)benzene hydrochloride | 2.50 | 5.00 | 7.50 | 10.00 |
| Sodium chloride, USPXVIII | 8.53 | 8.07 | 7.70 | 7.10 |
| Epinephrine, USPXVIII | 0.0050 | 0.0050 | 0.0050 | 0.0050 |
| Sodium metabisulfite | 0.50 | 0.50 | 0.50 | 0.50 |
| Sodium hydroxide, 2N | If necessary to adjust pH | | | |
| Hydrochloric acid, 2N | If necessary to adjust pH | | | |
| Water for injection, USPXVIII | Sufficient amount to make 1000 ml | | | |

The active ingredient of the solutions above can be replaced by for example 1-isobutoxy-2-(2'-diisopropylaminoethoxy)-benzene hydrochloride.

EXAMPLE 10

This example illustrates pharmaceutical compositions for surface anesthesia by epicutaneous application to intact skin. Solutions containing 5 or 10% 1-n-butoxy-2-(2'-diisopropylaminoethoxy)-benzene (base or hydrochloride salt) may be prepared by mixing according to the following table:

| Component | Amount ~5% | ~10% | ·10% |
| --- | --- | --- | --- |
| 1-n-Butoxy-2-(2'-diisopropyl-aminoethoxy)benzene | 50 g(base) | 100 g(base) | 100 g(salt) |
| Glycerol | 250 ml | 250 ml | — |
| Isopropanol | 650 ml | 650 ml | — |
| Water | 100 ml | 100 ml | Sufficient amount to make 1000 ml |

The active ingredient of the solutions above can be replaced by for example 1-n-propoxy-2-(2'-diisopropylaminoethoxy)-benzene.

Biological tests

A. Guinea-pigs (Dunkin-Hartley, males, 4–6 weeks of age 350±50 g) were shaved and depilated. A gauze folded twice (23 mm diameter) was put into the test solution and thereafter in a plastic cup (outer diameter 26 mm, inner diameter 24 mm, inner height 4 mm). The cup with the gauze saturated with test solution was attached to the back of the animal as an occlusive dressing fastened with plaster (25 mm width) wound around the body). The time of contact was 30 min. After the end of the contact time the site of contact was washed and marked with a fatty chalk. With a sharp instrument (e.g. cannula or a pair of tweezers) the place was pricked six times and registering was made as in the intracutaneous wheal test (Bülbring-Wajda: J. Pharmacol., 1945, 85, p 78) on the back of the guinea-pig, i.e. by registering the presence or absence of a characteristic ripple of the skin of the back of the animal. Every pricking which gives no skin contraction was counted. The test was repeated at regular intervals of 5 min, during an interval of 30 min from the end of the application period. The test gives an indication of onset time, depth and duration of block. The percentage block during the 25 min testing period was used as an index for efficiency. The test solution consisted of the test compound (base) dissolved to 10% (w/v, g/ml) in a mixture of isopropanol (65%: v/v), glycerol (25%: v/v) and water (10%: v/v). The results from these tests are depicted in the following table:

| Compound according to Example No. | Code | Local anesthetic efficiency % (± s.e.m.) |
| --- | --- | --- |
| 1 | RAP 411 | 99.3 ± 0.7 |
| 2 | RAP 406 | 98.6 ± 0.8 |
| 3 | RAP 407 | 97.2 ± 2.8 |
| 4 | RAP 409 | 97.2 ± 2.8 |
| 5 | RAP 413 | 75.7 ± 9.4 |
| 6 | RAP 431 | 79.2 ± 12.6 (time of contact: 15 min) |
| — | RAP 419 | 0 |

The compound RAP 419 is o-methoxy-(diethylaminoethoxy)-benzene and belongs to the prior art (cp the first page of this specification).

The compound according to Example 1 (RAP 411) was tested also with varying concentrations and in the form of a hydrochloride salt in aqueous solution. At these tests it was found that 5% RAP 411 base in the alcoholic mixture, or 10% RAP 411 hydrochloride in aqueous solution gave complete anesthesia during at least 30 min.

The above test results mean that compounds according to the invention are very strong surface anesthetics, capable of giving complete anesthesia on application to intact skin. This is further illustrated by results obtained with lidocaine base (diethylaminoacet-2,6-xylidide) under identical experimental conditions. A solution of 20% lidocaine base in the same alcoholic mixture as used in the above test gave a local anesthetic effect of 38.3 ∓ 4.0%. Thus, even when used in twice the concentration the effect produced by lidocaine was much weaker than that of the new compounds. Furthermore the new compounds are effective even when applied in the form of a salt in aqueous solution to the intact skin.

B. The compounds according to the invention were also tested as to onset and duration of local anesthetic effect at parenteral administration (infiltration anesthesia). The test was carried out as described by L. F. Shackell (Anesth. Analg. 14 (1935) 20–22: "Test of local anesthetics by sciatic nerve blocks in the intact guinea-pig"). Four animals were used at each test. The results are depicted in the following table:

| Compound No. and Code | Conc. % | pH | Motor paralysis Onset (min) | Motor paralysis Duration (min) | Flexion reflex block Onset (min) | Flexion reflex block Duration (min) |
|---|---|---|---|---|---|---|
| 1 (RAP 411) | 0.5 | 6.0 | 1 | 231∓10 | 1 | 177∓8 |
| Ref. | 0.5 | 6.0 | 1 | 131±13 | 1–2 | 84±17 |
| 3 (RAP 407) | 0.5 | 6.6 | 1–2 | 200±28 | 1–2 | 180±32 |
| 5 (RAP 413) | 0.5 | 7.0 | 1 | 214±26 | 1 | 115±8 |
| Ref. | 0.5 | 6.8 | 1–2 | 112±8 | 1–3 | 83±20 |
| 6 (RAP 431) | 0.5 | 7.3 | 1 | 167±4 | 1 | 138±10 |
| -(RAP 419: prior art) | 0.5 | 7.4 | | 0 | | 0 |
| Lidocaine | 2.0 | 6.9 | 1 | 78±5 | 1–2 | 57±7 |

The reference compound being used at this test is 2-(N-ethyl-n-propylamino)-2',6'-n-butyroxylidide (etidocaine). This compound is a modern long-acting local anesthetic agent (Lund et al: Anesthesia and Analgesia: Vol 52, No. 3, p 482–494 (1973). From the above table it can be concluded that compounds according to the invention can give a morelong-acting local anesthetic effect than etidocaine, and also a much more long-acting effect than lidocaine.

C. The acute toxicity for the base forms of a number of the new compounds were tested in mice. From the table below it can be seen that the compounds according to the invention are somewhat more toxic than the well-known short-acting local anesthetic lidocaine, but clearly less toxic than etidocaine. The value for lidocaine and etidocaine are taken from the work of Adams et al (J. Pharm. Sci Vol 61, p 1829–1831, 1973).

Table

| | Acute toxicity LD 50 (base) mg/kg | |
|---|---|---|
| Compound No. and Code | i.v. | s.c. |
| 1 (RAP 411) | 15 | 250 |
| 3 (RAP 407) | 14 | 300 |
| 4 (RAP 409) | 18 | — |
| 5 (RAP 413) | 14 | — |
| 6 (RAP 431) | 9 | — |
| Etidocaine | 7 | 99 |
| Lidocaine | 26 | 211 |

We claim:
1. A compound of the formula

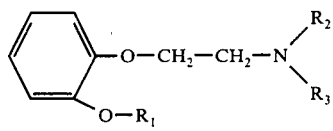

and pharmaceutically acceptable acid addition salts thereof, in which formula $R_1$ represents an alkyl group selected from the group consisting of n-propyl, n-butyl and i-butyl, $R_2$ and $R_3$ are the same and are selected from the group consisting of ethyl and i-propyl.

2. A compound according to claim 1, wherein $R_2$ and $R_3$ are i-propyl.

3. A compound according to claim 1; 1-n-butoxy-2-(2'-diisopropylaminoethoxy)-benzene.

4. A compound according to claim 1; 1-n-propoxy-2-(2'-diisopropylaminoethoxy)-benzene.

5. A compound according to claim 1; 1-i-butoxy-2-(2'-diisopropylaminoethoxy)-benzene.

6. A compound according to claim 1; 1-i-butoxy-2-(2'-diethylaminoethoxy)-benzene.

7. A compound of the formula

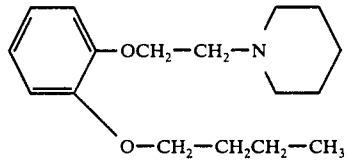

8. A local anesthetic composition containing as an active ingredient a therapeutically effective amount of a compound according to claim 1 together with a pharmaceutically acceptable carrier.

9. A local anesthetic composition containing as an active ingredient a therapeutically effective amount of a compound according to claim 2 together with a pharmaceutically acceptable carrier.

10. A local anesthetic composition containing as an active ingredient a therapeutically effective amount of a compound according to claim 3 together with a pharmaceutically acceptable carrier.

11. A local anesthetic composition containing as an active ingredient a therapeutically effective amount of a compound according to claim 4 together with a pharmaceutically acceptable carrier.

12. A local anesthetic composition containing as an active ingredient a therapeutically effective amount of a compound according to claim 5 together with a pharmaceutically acceptable carrier.

13. A local anesthetic composition containing as an active ingredient a therapeutically effective amount of a compound according to claim 6 together with a pharmaceutically acceptable carrier.

14. A local anesthetic composition containing as an active ingredient a therapeutically effective amount of a compound according to claim 7 together with a pharmaceutically acceptable carrier.

15. A method for producing local anesthesia, the method comprising administration to mammals, including humans, of a therapeutically effective amount of a compound according to claim 1.

16. A method for producing local anesthesia, the method comprising administration to mammals, including humans, of a therapeutically effective amount of a compound according to claim 2.

17. A method for producing local anesthesia, the method comprising administration to mammals, including humans, of a therapeutically effective amount of a compound according to claim 3.

18. A method for producing local anesthesia, the method comprising administration to mammals, including humans, of a therapeutically effective amount of a compound according to claim 4.

19. A method for producing local anesthesia, the method comprising administration to mammals, including humans, of a therapeutically effective amount of a compound according to claim 5.

20. A method for producing local anesthesia, the method comprising administration to mammals, including humans, of a therapeutically effective amount of a compound according to claim 6.

21. A method for producing local anesthesia, the method comprising administration to mammals, including humans, of a therapeutically effective amount of a compound according to claim 7.

* * * * *